United States Patent [19]
Whitham

[11] Patent Number: 5,270,042
[45] Date of Patent: Dec. 14, 1993

[54] MEDICINAL SALVE COMOPSITION

[76] Inventor: Juanita Whitham, 1724 N. Heights Dr., Sheridan, Wyo. 82801

[21] Appl. No.: 21,141

[22] Filed: Feb. 23, 1993

[51] Int. Cl.⁵ .............................................. A61K 6/00
[52] U.S. Cl. ..................................... 424/401; 424/47; 424/441; 424/443
[58] Field of Search ................ 424/401, 443, 441, 47; 514/256

[56] References Cited

U.S. PATENT DOCUMENTS

| | | | |
|---|---|---|---|
| 3,943,248 | 3/1976 | Shulman | 424/196 |
| 4,401,651 | 8/1983 | Knutson | 424/80 |
| 4,504,470 | 3/1985 | Uda et al. | 514/19 |
| 4,725,438 | 2/1988 | Leazer | 424/195.1 |
| 4,883,664 | 11/1989 | Sharkey | 424/196.1 |
| 4,904,674 | 2/1990 | Martin et al. | 514/337 |
| 5,116,600 | 5/1992 | Fujii et al. | 514/256 |

*Primary Examiner*—Thurman K. Page
*Assistant Examiner*—W. Benston
*Attorney, Agent, or Firm*—Richard C. Litman

[57] ABSTRACT

A medicinal salve composition and method for the topical treatment of a variety of deleterious skin conditions. The salve composition comprises a mixture of powdered sugar, boric acid, soybean oil, and a pharmaceutically-acceptable ointment base. The essential components of the present composition are combined in such relative proportionalities so as to form a homogeneous mixture having a consistency suitable for application to burns, wounds, lesions, and other skin traumas.

4 Claims, No Drawings

MEDICINAL SALVE COMOPSITION

BACKGROUND OF THE INVENTION

1. Field of the Invention

This invention relates generally to a salve composition having medicinal properties in the treatment of skin disorders. More particularly, the present invention pertains to a medicinal salve composition which includes sugar as a therapeutically active ingredient for topically treating burns, wounds, lesions, and other skin traumas.

2. Description of the Prior Art

Numerous salve or ointment compositions are available for the topical treatment of a variety of deleterious skin conditions including open wounds and burns. Amongst the numerous substances tested as active ingredients in promoting the healing of wounds, only a small number of those additives have been shown to be more effective than the ointment carriers alone. For example, various herbs and plant extracts have been known to be used in salves and/or ointment preparations as therapeutic agents for healing wounds and treating minor burns. Typical of such preparations claiming some medicinal value are disclosed in U.S. Pat. Nos. 4,725,438 to Leazer and U.S. Pat. No. 4,883,664 to Sharkey. The patent to Leazer describes an aloe vera ointment which is effective in treating topical lesions, and the Sharkey patent discloses a medicinal salve for the treatment of burns, scalds, insect bites and the like comprising olive oil, beeswax, camphor, pine rosin, and lanolin. However, it is difficult to maintain the therapeutic effectiveness of many of these additives, and the unstable medicaments can not be used on a long term basis without undesirable side effects.

It has also been suggested in the prior art that free granulated sugar and sugar products such as honey and molasses have been used for centuries in treating wounds and burns. More recently, U.S. Pat. No. 4,401,651 to Knutson discloses a wound-healing composition containing polyvinylpyrrolidone-iodine as the antifungal/antibacterial agent and granulated sugar in a suitable carrier. However, the components of this patented composition tend to separate upon standing or storage and must be redispersed prior to use. Also, the sugar/anti-infective composition of this patent tends to enhance bleeding and its application to bleeding wounds is not recommended until hemostatis is assured. In addition, the antifungal/antibacterial component of the reference formulation is a relatively complex or costly pharmaceutical additive, and the compounding of such formulations has proved to be a relatively involved, time-consuming procedure.

SUMMARY OF THE INVENTION

Accordingly, it is an object of the present invention to provide a medicinal salve or ointment composition which is safe and effective in topically treating a variety of wounds and other lesions.

It is a further object of the invention to provide a hemostatic wound-healing salve which is stable and does not require expensive ingredients or complicated preparation procedures.

These and other objects are accomplished in accordance with the present invention which provides a salve composition consisting essentially of a mixture of powdered sugar, boric acid, soybean oil, and a pharmaceutically-acceptable ointment base. The essential components of the present composition readily intermix to form a homogeneous mixture having a consistency suitable for application to burns, wounds, lesions, and other skin traumas. The present components are combined in such relative proportionalities so as to bring about a marked wound healing effect which exceeds that which would normally be expected by merely adding the individual constituents together.

The foregoing and other aspects, advantages and objects of the invention may be more fully appreciated by reference to the following detailed description.

DETAILED DESCRIPTION OF THE PREFERRED EMBODIMENTS

In accordance with one embodiment of the present invention, the medicinal salve composition is a substantially homogeneous admixture consisting essentially of the following ingredients in the following relative proportions:

about 45–55% by volume of powdered sugar,
about 10–15% by volume of boric acid,
about 20–30% by volume of soybean oil, and
about 10–15% by volume of the weight of the ointment base.

The powdered sugar ingredient is produced by grinding or pulverizing granulated sugar to a finely divided state. This sugar product is commercially known as confectioner's or icing sugar and may contain up to 3 per cent cornstarch to prevent caking. The powdered sugar is substantially uniformly dispersed throughout the salve composition to provide an improved medicinal effect, notably by providing optimum absorption of this therapeutically active ingredient to promote rapid wound healing. Thus, it has been determined that decreasing the concentration of this essential component decreases the effectiveness of the salve. This sugar ingredient, together with the boric acid component of the present composition, also provides antibacterial activity. The soybean oil component is believed to provide the present composition with bactericidal as well as antiseptic properties. It will be appreciated that all of these ingredients are relatively inexpensive and readily available commercially.

The ointment base should be essentially non-toxic, odorless, relatively inexpensive and pharmaceutically safe for administration directly to open wounds, for example. Petrolatum, which is a neutral unctuous substance and commercially available under the trademark Vaseline, serves as the preferred base.

In accordance with a preferred embodiment of the present invention, the medicinal salve composition consists essentially of about 50% by volume of powdered sugar, about 12.5% by volume of boric acid, about 25% by Volume of soybean oil, and about 12.5% by volume of the weight of petrolatum.

The preparation of the present salve compositions may be achieved very economically and rapidly. In preparing the preferred embodiment of the present invention, about 2 part by volume of the soybean oil and about 1 part of petrolatum are intermixed by heating with attendant stirring to form a liquid solution. About 4 parts by volume of powdered sugar is then added to the heated solution with agitation until the powder is completely dissolved and lump free. The resultant solution becomes viscous in consistency and about 1 part by volume of boric acid is finally added and the four ingredients are thoroughly mixed together to form an intimate salve mixture. After cooling to ambient temperatures, the uniform mixture may then be placed in any suitable container, preferably a sealable jar or tube, until ready for use.

The salve mixtures of the present invention maintain their effectiveness for extended periods of time and do not liquefy on storage nor do the powdered sugar particles settle out. It has been found that the present salves are effective in promoting the healing of a wide variety of wounds which involve injury or trauma to the skin. Injuries which have been effectively treated with this salve composition include abrasions; common burns, including sunburn; incised, lacerated, open, penetrating and puncture wounds; open skin lesions such as decubitus ulcers (also called bedsores or pressure sores); and other deleterious skin conditions.

The present medicinal salve is particularly adapted for application in effective amounts directly to the area of the skin requiring treatment. In a typical dressing procedure, any previously applied dressing is first removed, and the treatment area is gently cleaned and then dried. The salve is applied sparsely or liberally to the wound, burn, lesion or other skin injury to be treated, completely covering the treatment area. Application may be performed by hand, but is preferably conducted with a suitable medical applicator or swab. Bandages or other protective wrappings may be applied to cover the treated area if desired. Alternatively, the salve can be spread onto gauze, sponge dressing or similar material and the salve-containing dressing can then be applied to the wound surface. This dressing procedure may be repeated two to four times a day until the skin condition has healed. However, more frequent application is also contemplated. For example, in the treatment of severe skin injuries, it may be desirable to continuously maintain the salve composition on the injured area during healing. Use may also be for extended periods, including months, without any adverse side effects.

Advantageously, the salve composition of the present invention is water repellent and readily adheres to the affected area being treated. Further, the salve does not permanently stain clothing with ordinary usage. The salve provides a protective coating that enables the natural healing process to occur and prevents any additional irritation to the affected area. No adverse side effects from extended use were observed in a human test subject using the salve daily for over a year. The essential components of the salve composition combine to produce a certain synergistic effect, whereby rapid, scar-free healing is facilitated and superficial infection is suppressed. Further, since the present salve tends to arrest wound bleeding, a hemostatic agent becomes unnecessary and the salve can be applied to bleeding wounds within minutes after injury to assist in securing hemostasis.

The following example is given to further illustrate the present invention. All relative proportions are set forth as percentages by volume unless otherwise specifically indicated.

EXAMPLE

A composition in the form of a homogeneous salve is prepared according to the invention as described hereinabove by mixing the following ingredients:

| INGREDIENT | VOL. PERCENT |
|---|---|
| Powdered sugar | 50.0 |
| Boric acid | 12.5 |
| Soybean oil | 25.0 |
| Petrolatum | 12.5 |

The above salve composition was employed as a medicinal preparation to treat a test subject suffering from severe lesions on the hands, accompanied by intense itching. The test subject is an elderly woman whose condition was diagnosed by physicians as solar dermatitis, but proved untreatable with conventional medicaments such as cortisone cream. The salve was applied twice daily to the affected areas of the hands. The subject experienced immediate relief from itching after the first application and a noticeable decrease in the number and severity of the lesions was observed within days after the initial treatment.

It should be understood that there may be various changes and modifications of the representative embodiments herein chosen for purposes of description without departing from the spirit and scope of the invention. Accordingly, the foregoing descriptions are not to be interpreted as restrictive of the invention beyond that necessitated by the following claims.

I claim:

1. A medicinal salve composition for topically treating burns, wounds, lesions, and other skin traumas, said salve composition consisting essentially of a substantially homogeneous admixture of:
   about 45-55% by volume of powered sugar,
   about 10-15% by volume of boric acid,
   about 20-30% by volume of soybean oil, and
   about 10-15% by volume of the weight of an ointment base.

2. The composition according to claim 1 wherein said ointment base is petrolatum.

3. The composition according to claim 2 which consists essentially of about 50% by volume of powered sugar, about 12.5% by volume of boric acid, about 25% by volume of soybean oil, and about 12.5% by volume of the weight of petrolatum.

4. A method for treating burns, wounds, lesions, and other skin traumas which comprises topically applying to the affected skin area an effective amount of the salve composition of claim 1.

* * * * *